US008128550B2

(12) United States Patent
Loeb et al.

(10) Patent No.: US 8,128,550 B2
(45) Date of Patent: *Mar. 6, 2012

(54) EXTERNAL COUNTER PULSATION TREATMENT

(75) Inventors: Marvin P. Loeb, Laguna Woods, CA (US); Ginger Johnson, Muskegon, MI (US); John McCallum, Vista, CA (US)

(73) Assignee: Cardiomedics, Inc., Irvine, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 12/386,093

(22) Filed: Apr. 14, 2009

(65) Prior Publication Data

US 2009/0247809 A1 Oct. 1, 2009

Related U.S. Application Data

(63) Continuation-in-part of application No. 10/938,155, filed on Sep. 10, 2004, now Pat. No. 7,517,312, which is a continuation-in-part of application No. 10/681,812, filed on Oct. 7, 2003, now Pat. No. 7,244,225.

(51) Int. Cl.
*A61N 1/362* (2006.01)

(52) U.S. Cl. .......................................................... 600/16

(58) Field of Classification Search ............... 600/16–17
See application file for complete search history.

(56) References Cited

U.S. PATENT DOCUMENTS

| | | | | |
|---|---|---|---|---|
| 7,244,225 | B2 * | 7/2007 | Loeb et al. | 600/17 |
| 7,517,312 | B2 * | 4/2009 | Loeb et al. | 600/16 |
| 2002/0107461 | A1 * | 8/2002 | Hui | 601/149 |
| 2003/0216651 | A1 * | 11/2003 | Burns et al. | 600/483 |

* cited by examiner

*Primary Examiner* — Eric D. Bertram

(74) *Attorney, Agent, or Firm* — Olson & Cepuritis, Ltd.

(57) ABSTRACT

A method for treating patients suffering from left ventricular dysfunction is disclosed. The method involves applying, during diastole, for a time period of about one hour, at least five days each week for at least about six weeks, an incrementally increasing external therapeutic pressure sequentially to the patients' lower extremities from first the calves, then the thighs and last the buttocks. The initial hourly treatments are carried out at a peak diastolic/systolic pressure ratio (D/S Ratio) in the range of about 0.4:1 up to about 0.9:1, depending on the patient's left ventricular ejection fraction. The D/S Ratio is increased slightly during the next set of hourly treatments, the D/S Ratio is again increased slightly during the next following set of hourly treatments, the D/S Ratio is again increased slightly during the next set of hourly treatments, and finally the D/S Ratio is increased slightly and maintained during the remaining set of hourly treatments. The patient's cardiopulmonary functions preferably are monitored to determine if additional external therapeutic pressure treatments are needed.

24 Claims, No Drawings

EXTERNAL COUNTER PULSATION TREATMENT

CROSS-REFERENCE TO RELATED APPLICATIONS

This application is a continuation-in-part of U.S. Ser. No. 10/938,155 filed on Sep. 10, 2004, now U.S. Pat. No. 7,517,312, which, in turn, is a continuation-in-part of U.S. Ser. No. 10/681,812, filed on Oct. 7, 2003, now U.S. Pat. No. 7,244,225 issued on Jul. 17, 2007, all incorporated herein by reference.

FIELD OF INVENTION

This invention relates to a non-invasive treatment for congestive heart failure and other conditions typified by a low left ventricular ejection fraction (LVEF).

BACKGROUND OF INVENTION

Congestive Heart Failure (CHF) is one of the major causes of death in the United States. CHF severely affects an estimated two million people in the United States and causes approximately 400,000 deaths per year. CHF is also one of the most significant burdens on health care costs. It is estimated that the costs to Medicare for the treatment of CHF is about $40 billion each year.

Current treatments for CHF include pharmaceuticals such as ACE inhibitors, Angiotensin II receptor blocker, and beta blockers. These pharmaceuticals have only moderately reduced mortality rates, however. Additionally they pose risks of adverse drug reactions or interactions.

Invasive therapies such as implantable defibrillators and dual chamber, cardiac "resynchronization" pacemakers are also utilized to manage CHF patients whose hearts have a rhythm abnormality, about 30% of CHF patients. These therapies are extremely expensive (implantation of such devices in the U.S. currently costs $50,000 or more), require surgery and have shown only a reduction in mortality of about 50% from the American Heart Association's published figure of 18.8% annual mortality from CHF in the United States.

External counterpulsation (ECP) is currently gaining acceptance as an effective therapy for angina and CHF. "Counter Pulsation" decreases cardiac workload and improves heart function by increasing blood flow through the coronary vessels using a series of cuffs, fastened about the legs and buttocks, which contain inflatable bladders. "External" means that the treatment is applied to the exterior of the of the patient's body and is non-invasive. Surgery, anesthesia and injections are not required.

ECP is a safe and effective treatment to assist circulation, particularly in the treatment of ischemic heart disease. It has also been shown to increase diastolic pressure and flow through the coronary arteries, cause angiogenesis by the release of naturally occurring angiogenic growth factors, reduce systolic pressure and the work effort of the heart, induce endothelial remodeling, improve vessel elasticity, produce neurohormonal benefits and release nitrous oxide, a potent vasodilator.

The ECP treatment system compresses the legs from the calves through the thighs, and the buttocks, by sequentially inflating sets of bladders encased in flexible, fabric cuffs during the resting phase of the heart cycle (diastole). This results in the movement of blood from the legs and buttocks toward the heart through both the arterial and the venous systems.

Each wave of pressure is electronically timed to the patient's electrocardiogram (ECG) so that blood flow to the heart is increased during the time period the heart is relaxing (diastole). Before the heart begins to contract again (systole), the pressure is rapidly released. This lowers resistance in the blood vessels of the legs and the buttocks, enabling blood to be pumped more easily from the heart, decreasing the amount of work required of the heart muscle. Also, blood forced up the veins by ECP returns to the heart and is termed "preloading" the heart. These effects are evidenced by a reduction in the patient's systolic pressure.

The aortic valve is the heart valve through which blood leaves the left ventricle, the main pumping chamber of the heart, and which prevents back flow into the left ventricle. During diastole, the aortic valve is closed. The coronary arteries open off the aorta, above the aortic valve, and the pressure applied to the lower extremities drives blood up the arteries into the aorta and, since the aortic valve is closed, the blood exits the aorta through the coronary arteries, expanding the heart's networks of tiny auxiliary blood vessels called "collaterals". This is evidenced by an increase in the patient's diastolic pressure. The volume of blood flowing to the heart muscle is thus increased.

The typical ECP treatment regimen for chronic angina patients whose left ventricular ejection fraction (LVEF) is normal (50% to 70%) is 35 hours of treatment, usually one-hour per day, five days per week for seven weeks. Alternatively, ECP may be applied for one-hour per day, six days a week for six weeks, a total of 36 hours. While not as desirable as the above-regimens, a 2-hour per day regimen can also be utilized, which reduces the time to completion to 3 or 3½ weeks.

Pressure is typically applied to produce a peak diastolic pressure to peak systolic pressure ratio (D/S Ratio) of 1.5:1 to 2:1 or higher in the treatment of such chronic angina patients. The duration of treatment and rest intervals depend on the patient's condition, the degree of augmentation of diastolic pressure to systolic pressure obtained, the patient's LVEF, patient tolerance to ECP and like indications.

Currently practiced ECP methods, such as those used in the treatment of chronic angina with substantially normal LVEF (i.e., at D/S Ratio of 1.5:1 to 2:1 or higher), can cause excessive pre-loading of the heart. If the patient also suffers from CHF and exhibits a LVEF less than 50%, the heart cannot pump out or "eject" a sufficient amount of blood. This causes blood to "pool" or build up in the blood vessels of the lungs, abdomen and extremities, as well as fluid to build-up in the calves, ankles and feet. The heart muscle necessarily works harder and thickens, which further reduces its pumping efficiency. As a result, more fluid builds up in the lungs, making it difficult for the patient to breathe. A recurrence or worsening of heart failure or even death can result.

The ECP therapy method disclosed herein seeks to use a graduated series of steps, in which the D/S Ratio is periodically increased, starting at a relatively low pressure to avoid the undesirable consequences of the currently practiced high pressure ECP regimen therapy for angina. This graduated low pressure ECP regimen can benefit CHF and heart attack patients, as well as those with other conditions that cause a low LVEF such as ischemic strokes, acute renal or hepatic failure, cardiogenic shock, and the like. Such graduated low pressure ECP regimen therapy leads to a substantial long-term reduction in hospitalization and mortality, as well as an improvement in the condition and quality of life of the patient.

The method disclosed herein also seeks to include a group of patients that are excluded from the current high pressure ECP Regimen therapy for angina; patients with low LVEF.

There is thus a need for a non-invasive means to effectively treat and manage patients with CHF and other ailments exhibiting a decrease in the volume of blood flow the heart can eject on such compression, such as the ECP Regimen therapy disclosed herein.

SUMMARY OF THE INVENTION

The present invention is eminently well suited for treating patients exhibiting left ventricular dysfunction and having a left ventricular ejection fraction of at least 15%, but less than normal. The method comprises a daily application of external therapeutic pressure to the lower extremities of a patient during diastole, i.e., during the resting phase of the cardiac cycle. The external therapeutic pressure is applied sequentially to lower extremities of the patient, i.e., first to the patient's calves, next to the patient's thighs and then to the patient's buttocks. The present method can be used to treat congestive heart failure, angina patients with CHF and LVEF's less than normal, heart attacks, cardiogenic shock, ischemic stroke, cardiomyopathy, post-heart transplant cardiac dysfunction, post-cardiac arrest, cardiac rhythm dysfunction, heart trauma, heart infection, post-acute myocardial infraction dysfunction, acute renal or hepatic failure, peripheral artery disease, edema, cognitive deficits, hearing acuity, sexual dysfunction and the like.

The treatment regimen for CHF and angina patients with a left ventricular ejection fraction of at least 15 percent comprises, applying during diastole, daily, for at least five days a week, for at least six weeks, for a time period of about one-hour, incrementally increasing external therapeutic pressure application beginning with at least one one-hour treatment to produce a D/S Ratio in the range of about 0.4:1 up to about 0.9:1. The next set of one-hour treatments is given to produce a D/S Ratio in the range of about 0.5:1 up to about 1:1. Thereafter, at least one additional set of one-hour treatments is applied to produce a D/S Ratio in the range of about 0.6:1 up to about 1:1 depending upon the patients initial LVEF range. During the ECP Regimen, the initial hourly treatment D/S Ratio is incrementally increased from the initial D/S Ratio by a value of about 0.1 for each subsequent set of hourly treatments.

In order to achieve these relatively low D/S ratios, the ECP device utilized must be able to stably produce applied pressures in the range of about 10 to about 90 millimeters of mercury (Hg) and higher, preferably at least about 40 mm of Hg. Preferably the applied pressure should not exceed about 240 millimeters of mercury.

DETAILED DESCRIPTION OF PREFERRED EMBODIMENT

Abbreviations and Acronyms

AMI=Acute Myocardial Infarction (Heart Attach)

CABG=Coronary Artery Bypass

CCSF=Canadian Cardiovascular Society Function

CHF=Congestive Heart Failure

D/S Ratio=Peak Diastolic to Peak Systolic Pressure Ratio

ECP=External Counterpulsation

LVEF=Left Ventricular Ejection Fraction

NYHA=New York Heart Association

"Congestive heart failure" is a condition in which the heart cannot pump enough blood to the lungs and body's other organs, which in turn leads to fluid retention. This condition results, inter alia, from diastolic heart dysfunction. Heart failure of diastolic etiology is more common than heart failure of systolic etiology.

"Left ventricular ejection fraction (LVEF)" as used herein and in the appended claims is the percentage of the end diastolic volume of blood ejected during systole and is calculated as follows:

$$LVEF = \frac{\text{end diastolic volume} - \text{end systolic volume}}{\text{end diastolic volume}} \times 100$$

In the data reported herein below, LVEF was assessed using either nuclear imaging or echocardiography (ultrasound, imaging), pre- and one-year post treatment.

External Counter Pulsation (ECP) is a non-invasive version of the intra-aortic balloon pump. ECP is utilized in the present method to move a relatively large volume of blood to the heart, while decreasing cardiac workload (systolic pressure) and increasing diastolic pressure.

When ECP is administered to CHF patients at the compression pressures, delay times and compression durations common to the treatment of Angina (usually at a D/S Ratio of 1.5:1 to 2:1 or higher), some CHF patients, particularly those with relatively low ejection fractions, cannot eject the increased volume of blood delivered to the heart. Some patients do well for the first 5 to 10 hours of ECP therapy at such D/S Ratios, but thereafter their CHF symptoms worsen, they may require hospitalization, and death can result.

These problems can be avoided by daily one-hour ECP treatments at relatively lower-initial D/S Ratios used with patients with very low ejection fractions, i.e., about 15% to 20%. ECP at somewhat higher D/S Ratios is then applied during the following treatment hours of the ECP Regimen. This regimen, utilizing a gradual increase in D/S Ratio from an uncommonly low, starting level, is known as the HeartSmart® Graduated™ ECP Regimen (Cardiomedics, Inc., Irvine, Calif.).

CHF patients with an ejection fraction less than 15% are in an extremely fragile condition and are ordinarily not suitable candidates for ECP.

If the CHF patient has an ejection fraction of 15% to 20%, in addition to optimal timing of compression, ECP more preferably is applied to produce a D/S Ratio of about 0.4:1 for at least the first hour of ECP (some patients may require more than one hourly treatment at D/S Ratio of 0.4), next pressure is increased to produce a D/S Ratio of about 0.5:1 for at least the next three hours of ECP, next pressure is increased to produce a D/S Ratio of about 0.6:1 for the next five hours, thereafter pressure is increased to maintain a D/S Ratio of about 0.7:1 for the next 10 hours of ECP, and then pressure is increased as needed to maintain a D/S Ratio of 0.8:1 for the balance of the Graduated ECP Pressure Regimen, for an average D/S Ratio of about 0.7:1 over the ECP Regimen, thereby training the heart to gradually eject a greater volume of blood.

If the CHF patient's ejection fraction is 20% to 30%, in addition to optimal timing of compression, ECP more preferably is applied to produce a D/S Ratio of about 0.5:1 for at least the first hour of ECP, next pressure is increased to produce a D/S Ratio of about 0.6:1 for at least the next three hours of ECP, for the next five hours, the pressure is increased to produce a D/S Ratio of about 0.7:1, thereafter pressure is increased sufficient to maintain a D/S Ratio of about 0.8:1 for the next 10 hours of ECP, and then pressure is increased as needed to maintain a D/S Ratio of about 0.9:1 for the remainder of the Graduated ECP Pressure Regimen, for an average D/S Ratio of about 0.8:1, producing the same training effect on the heart.

If the CHF patient's ejection fraction is 30% to 40%, in addition to optimal timing of compression, ECP more preferably is applied to produce a D/S Ratio of about 0.6:1 for at least the first hour of ECP, next pressure is increased to produce a D/S Ratio of about 0.7:1 for at least the next three hours of ECP, next pressure is increased to produce a D/S Ratio of about 0.8:1 for the next five hours, and thereafter pressure is increased to maintain a D/S Ratio of about 0.9:1 for the next 10 hours of ECP, and then the pressure is increased as needed to maintain a D/S Ratio of about 1:1 for the balance of the ECP Regimen, for an average D/S Ratio of about 0.9:1.

For CHF patients exhibiting an ejection fraction of 40% to 50%, in addition to optimal timing of compression, ECP is more preferably applied to produce a D/S Ratio of about 0.7 for at least the first hour of ECP, next pressure is increased to produce a D/S Ratio of about 0.8 for at least the next three hours of ECP, next pressure is increased to produce a D/S Ratio of about 0.9:1 for the next five hours of ECP, next pressure is increased to produce a D/S Ratio of about 1:1 for the next 10 hours of ECP, and then the pressure is increased as needed to maintain a D/S Ratio of about 1.1:1 for the balance of the ECP Regimen.

In the treatment of heart attacks, ECP can be administered as soon as possible after the onset of symptoms for up to four hours at a time, with a 10-minute rest period after each hour of treatment. Post-discharge heart attack patients, especially those with residual chest pain or CHF symptoms, post-discharge cardiogenic shock patients, and heart transplant patients (after allowing sufficient time for healing) should receive at least 35 hours of ECP, as described above.

The lowest possible therapeutic pressure to achieve the D/S Ratio should be utilized. This gradual increase in the D/S Ratio allows the Graduated, Low Pressure ECP Regimen therapy to be utilized on patients with an ejection fraction as low as 15 percent.

Specifically, if the patient has an ejection fraction of about 15% to 20%, in addition to optimal timing of compression, ECP more preferably is applied at a pressure, usually starting at about 40 mm Hg., and gradually increased, if necessary, to produce a D/S Ratio of about 0.4:1 at least for the first hour of ECP, next the pressure is increased to produce a D/S Ratio of about 0.5:1 for at least the next three hours of ECP, during the next five hours of ECP pressure is applied to produce a D/S Ratio of about 0.6:1, thereafter pressure is increased to maintain a D/S Ratio of about 0.7:1 for the next ten hours of ECP, and during the remaining hours of ECP treatment pressure is applied to produce a D/S Ratio of about 0.8:1, thereby training the heart to gradually eject a greater volume of blood. Preferably, the foregoing regimen is carried out to produce an average D/S Ratio of about 0.7:1.

If the patient has an ejection fraction of 20% to about 30%, in addition to optimal timing of compression, ECP more preferably is applied at a pressure, usually starting out at about 40 mm of Hg., and gradually increased, if necessary, to produce a D/S Ratio of about 0.5:1 for at least the first hour of ECP, during at least the next three hours the pressure is increased to produce a D/S Ratio of about 0.6:1. Next, pressure is applied to produce a D/S Ratio of about 0.7:1 for the next five hours of ECP treatment. Thereafter, pressure is applied during the next 10 hours of ECP treatment to produce a D/S Ratio of about 0.8:1 and during the remaining hours of ECP, the pressure is applied to produce a D/S Ratio of about 0.9:1, thereby training the heart to gradually eject a greater volume of blood. Preferably, the foregoing regimen is carried out to produce an average D/S Ratio of about 0.8:1.

If the patient's ejection fraction is about 30% to 40%, in addition to optimal timing of compression, pressure, usually starting at about 40 mm Hg., and gradually increased, if necessary, is applied during ECP to produce a D/S Ratio of about 0.6:1 for at least the first hour of ECP, pressure is then increased to produce a D/S Ratio of about 0.7:1 for at least the next three hours, then pressure is increased to produce a D/S Ratio of about 0.8:1 for the next five hours and, thereafter, pressure is increased to produce a D/S Ratio of about 0.9:1 for the next ten hours of ECP, and finally pressure is applied during the remaining hours of ECP to produce a D/S Ratio of about 1:1, producing the same training effect on the heart. Preferably, the foregoing regimen is carried out to produce an average D/S Ratio of about 0.9:1.

If the patient's ejection fraction is about 40% to 50%, in addition to optimal timing of compression, ECP is applied at a pressure, usually starting at about 40 mm Hg., and gradually increased, as necessary, to produce a D/S Ratio of about 0.7:1 for at least the first hour of ECP, next pressure is increased to produce a D/S Ratio of about 0.8:1 for at least the next three hours of ECP, thereafter pressure is increased to maintain a D/S Ratio of about 0.9:1 for the next five hours of ECP, next the pressure is increased to produce a D/S Ratio of about 1:1 for the next ten hours, and then the pressure is increased as needed to maintain a D/S Ratio of about 1.1:1 for the remaining hours of ECP. Preferably, the foregoing regimen is carried out to produce an average D/S Ratio of about 1:1.

If the patient's ejection fraction is greater than about 50%, e.g., a patient suffering from angina or CHF with such a LVEF, in addition to optimal timing of compression, ECP is applied at a sufficient pressure during at least the first hour to achieve a D/S Ratio of about 0.9:1, during at least the next three hours, sufficient pressure is applied to obtain a D/S Ratio of 1:1, next pressure is increased to achieve a D/S Ratio of about 1.1:1 during the next five hours, during the next 10 hours pressure is applied to produce a D/S Ratio of about 1.2:1, and thereafter, for the remaining ECP therapy, pressure is delivered to achieve a D/S Ratio of about 1.3:1. Preferably, the foregoing regimen is carried out to produce an average D/S Ratio of about 1.2:1.

Some CHF patients may require more than 35 hours of the Graduated Low Pressure ECP Regimen, some up to about 60 hours, or more.

Once the initial ECP Regimen has been completed, a patient's cardiopulmonary indicators should be accessed, preferably by the CardiAssess® Cardio Pulmonary Diagnostic or CPD System, commercially available from Cardiomedics, Inc., Irvine, Calif. These indicators include ventilation efficiency/volume of $CO_2$ ($VE/VCO_2$ slope), the heart rate recovery time (bpm) after exercise (HRRtX), peak volume of $O_2$ ($pVO_2$), oxygen efficiency (OE) and chronotropic response index (CRI). A $VE/VCO_2$ slope of about 37 degrees or higher, a HRRtX of less than 17 beats per minute (bpm), a $pVO_2$ less than 7.4 ml beat, an OE less than 1.7 or chronotropic response index (CRI) less than 0.8 indicate impaired cardiopulmonary functions. If three of the five indicators suggest impaired cardiopulmonary functions, further diagnosis is indicated and additional hours of ECP therapy might be required or the entire 35 hour ECP Regimen might be repeated.

Following the initial ECP Regimen, the patient's $VE/VCO_2$ slope, HRRtX, $pVO_2$, OE and CRI, should be monitored, preferably quarterly. If a significant decline in the patient's cardiopulmonary functions occurs, additional hours of ECP treatment may be needed, or the 35-hour ECP Regimen may need to be repeated.

Furthermore, during the Graduated, Low Pressure ECP Regimen therapy, if a patient's $O_2$ saturation level drops below about 90 percent, the pressure applied to produce the desired D/S Ratio is increased. However, if the patient's $O_2$ saturation level rises above about 90 percent, the ECP treatment should be stopped.

ECP, applied by gradually increasing the D/S Ratio, causes a "training effect" on the heart, resulting in its beating more synchronously (similar to the effect of a dual chamber, cardiac resynchronization pacemaker) and promotes angiogenesis, endothelial cell remodeling, release of nitrous oxide (a potent vasodilator) and other benefits of ECP. As the patient's heart grows stronger and beats more efficiently, it can accept and eject successively larger volumes of blood.

Treatment and Follow-up. Data from the Cardiomedics ECP Patient Registry (sponsored by Cardiomedics, Inc. Irvine, Calif., USA) was used to examine the benefit and safety of ECP treatment with the sponsor's CardiAssist™ ECP System in 130 patients with NYHA Class I-IV CHF and concomitant CCSF Class III or IV angina pectoris (Angina) over a period of one year and to derive a preferred treatment protocol.

All of the patients received 35 ECP treatments (one-hour per day, 5 days a week over a seven-week period). The study included both male (104) and female (26) patients (age range 47-88). CCSF Class IV Angina was seen only in the NYHA Class IV CHF patients. All descriptive statistics are shown as means±1 SD.

Data was also analyzed on subgroups of 54, 40 and 36 patients who were treated at an average D/S Ratio of 0.7:1 (range 0.4 to 0.99:1), 1.08:1 (range 1.0 to 1.29:1), and 1.32:1 (range 1.3 to 1.6:1), respectively. In the 54 and 40 patient subgroups, ECP was applied pursuant to a proprietary ECP treatment protocol in which the ECP treatments were begun at low D/S Ratios and gradually increased to take advantage of ECP's "training effect" on the heart, which enables the heart to eject successively larger volumes of blood, versus the subgroup of 43 patients who were treated at an average D/S Ratio of 1.32:1 (range 1.30:1 to 1.60:1), which are used in the treatment of angina.

Data on the enrolled patients was collected at six clinical sites in the United States and entered into a standardized Excel® database. The final dataset was merged and transferred to a SPSS Version 12.0 statistical package. Data was analyzed on each group of CHF patients and comparisons made pre- and one-year post treatment. Measurements were expressed as mean±standard deviation. Individual variable differences from baseline to the end of the study period were determined, using the student t-test for numerical variables and the chi square test for categorical variables with significance at $p<0.05$.

Baseline Data:

Baseline characteristics of the three groups and the group as a whole are shown in Table I, below.

Of the 54 CHF patients in the Low D/S Ratio Group, 79.6% were male, and the mean age was 68.2±15.6. None (0%) had NYHA Class I CHF, 6 (11.1%) had Class II CHF, 42 (77.7%) had Class III CHF and 6 (11.1%) had Class IV CHF. 76.8% also had CCSF Class III Angina, and 24.3% also had CCSF Class IV Angina. Mean LVEF prior to ECP therapy was 32.6%±7%. History of CABG was present in 75.9% and PTCA in 90.7%.

Of the 40 CHF patients in the Mid D/S Ratio Group, 80.0% were male, and the mean age was 69.7±18.6. One (2.5%) had NYHA Class I CHF, 9 (22.5%) had Class II CHF, 24 (60.0%) had Class III CHF and 6 (15.0%) had Class IV CHF. 79.8% also had CCSF Class III Angina, and 14.3% also had CCSF Class IV Angina. Mean LVEF prior to ECP therapy was 31.3%±11%. History of CABG was present in 69.6% and PTCA in 90.7%.

Of the 36 CHF patients in the High D/S Ratio Group, 80.5% were male, and the mean age was 69.7±22.4. Two (5.5%) had NYHA Class I CHF, 13 (36.1%) had Class II CHF, 15 (41.6%) had Class III CHF and 6 (16.6%) had Class IV CHF. 74.5% also had CCSF Class m Angina, and 19.3% also had CCSF Class IV Angina. Mean LVEF prior to ECP therapy was 32.6%±20%. History of CABG was present in 78.9% and PTCA in 80.9%. All of the patients in the High D/S Ratio Group received medical therapy in accordance with accepted clinical practice.

All of the 130 patients received medical therapy in accordance with accepted clinical practice. None of the 130 patients had an LVEF exceeding 40% or less than 20%, and only three of the 130 patients were in NYHA Class I.

TABLE I

Baseline Characteristics

| | 54 Patients Low D/S Ratio Group | 40 Patients Mid D/S Ratio Group | 36 Patients High D/S Ratio Group |
|---|---|---|---|
| Average Age (yr): | 68.2 ± 15.6 | 69.7 ± 18.6 | 69.7 ± 22.4 |
| Gender: Male | 43 (79.6%) | 32 (80.0%) | 29 (80.5%) |
| Female | 11 (20.4%) | 8 (20.0%) | 7 (19.4%) |
| History of CABG: | 75.9% | 69.6% | 78.9% |
| History of PTCA: | 90.7% | 83.4% | 80.9% |
| Ejection Fraction: | 33% ± 7% | 31% ± 11% | 33% ± 20% |
| NYHA CHF Class I: | 0 (0%) | 1 (2.5%) | 2 (5.5%) |
| NYHA CHF Class II: | 6 (11.1%) | 9 (22.5%) | 13 (36.1%) |
| NYHA CHF Class III: | 42 (77.7%) | 24 (60.0%) | 15 (41.6%) |
| NYHA CHF Class IV: | 6 (11.1%) | 6 (15.0%) | 6 (16.6%) |
| ACE Inhibitors: | 81.5% | 55.0% | 74.4% |
| Beat Blockers: | 31.4% | 30.3% | 23.3% |
| Diuretics: | 68.5% | 55.0% | 75.0% |
| CC Blockers: | 11.1% | 15.2% | 9.3% |
| Nitroglycerin: | 66% | 62% | 61% |

Results:

Mortality: In the year following completion of the ECP therapy, of the 54 CHF patients in the Low D/S Ratio Group (average D/S Ratio 0.7:1), one (1.85%) died. Of the 40 CHF patients in the Mid D/S Ratio Group (average D/S Ratio 1.08:1), three (7.50%) died, and of the 36 CHF patients in the High D/S Ratio Group (average D/S Ratio 1.32:1), three (8.33%) died. Of the 130 patient group as a whole, seven (5.40%) died.

Mortality in the Low D/S Ratio Group of 1.85% was 90% less than the 18.8% annual mortality in NYHA Class I-IV CHF historical controls reported in the American Heart Association's 2002 Heart Failure and Stroke Statistical Update-2002, and 78.2% less than the 8.5 mortality (adjusted to a one-year period) reported in the Madit II Study (Moss, A. et al., Multicenter Automatic Defibrillator Implantation Trial II Investigators: Prophylactic implantation of a defibrillator in patients with myocardial infarction and reduced ejection fraction, *N. Eng. J. Med.* 2002; 346:877-883), which excluded NYHA Class IV CHF patients, who typically experience higher mortality.

The differences in mortality between the Low D/S Ratio Group to the Mid D/S Ratio Group, High D/S Ratio Group, the 130 patient group as a whole, the 8.5% annualized mortality of the above Madit II Study and the 18.8% mortality of the Heart Failure and Stroke Statistical Update were statistically significant ($p<0.0001$).

While the differences in mortality in the Mid D/S Ratio and High D/S Ratio Groups and the 130 patient group as a whole were comparable to the mortality of the aforementioned Heart Failure and Stroke Statistical Update, there was no statistical difference compared to the mortality of the above Moss Study.

Ejection Fraction: LVEF was assessed by echocardiography pre- and one-year post ECP treatment. Of the 53, 37 and 33 surviving patients in the Low, Mid and High D/S Ratio Groups and the 123 surviving patients of the group as a whole, LVEFs improved by 23.0%, 20.1%, 17.5% and 20.4%, respectively, one year after ECP therapy, from a mean of 32.6% to 40.1%, 31.3% to 37.5%, 32.6% to 38.3% and 32.3% to 38.9%, respectively. The difference in LVEFs in all three sub-groups and the entire 123 surviving patients were statistically significant ($p<0.05$). See Table II, below.

TABLE II

LVEF of Surviving Patients

| Group | TX Prior to ECP | One Year Post ECP Tx | % Change | p Value |
|---|---|---|---|---|
| Low D/S Ratio (53) | 32.6% ± 7.2 | 40.1% ± 26.9 | +23.0 | <.05 |
| Mid D/S Ratio (37) | 31.3% ± 11.6 | 37.5% ± 27.5 | +20.1 | NS |
| High D/S Ratio (33) | 32.6% ± 20.4 | 38.3% ± 14.7 | +17.5 | NS |
| Overall (123) | 32.3% ± 19.7 | 38.9% ± 28.1 | +20.4 | <.05 |

NYHA CHF Class: Of the 53 surviving patients in the Low D/S Ratio Group, NYHA Class improved by an average of 36.6% from a mean Class 3.0±1.0 pre-treatment to a mean Class 1.9±0.5 one year after ECP treatment ($p<0.0001$). Of the 37 surviving patients in the Mid D/S Ratio Group, NYHA Class improved by an average of 29.6% from a mean Class of 2.7±1.3 pre-treatment to a mean Class of 1.9±0.5 one year after ECP treatment ($p<0.005$). Of the 33 surviving patients in the High D/S Ratio Group, NYHA Class improved by an average of 29.6% from a mean Class of 2.7±1.3 pre-treatment to a mean Class of 1.9±0.5 one year after ECP treatment ($p<0.001$). The differences in NYHA Classes in all three of the sub-groups and the entire 123 surviving patients were statistically significant ($p<0.005$). See Table III, below.

TABLE III

CHF Classification of Surviving Patients

| Group | Class Pre Tx | One Year Post ECP Tx | % Change | p Value |
|---|---|---|---|---|
| Low D/S Ratio (53) | 3.0 ± 1.0 | 1.9 ± .5 | −36.6 | <.0001 |
| Mid D/S Ratio (37) | 2.7 ± 1.3 | 1.9 ± .5 | −29.8 | <.005 |
| High D/S Ratio (33) | 2.7 ± 1.3 | 1.9 ± .5 | −29.6 | <.01 |
| Overall (123) | 2.9 ± 1.1 | 1.8 ± .6 | −28.7 | <.001 |

Hospitalizations: Of the 54 Low D/S Ratio Group patients, the average incidence of all cause hospitalization, including terminal hospitalizations, was reduced by 85.7% from a mean admission rate of 2.8 per patient in the year prior to ECP treatment to 0.4 per patient in the following year. Of the 40 Mid D/S Ratio Group patients, the average incidence of all cause hospitalization, including terminal hospitalizations, was reduced by 82.6% from a mean admission rate of 2.3 per patient in the year prior to ECP treatment to 0.4 per patient in the following year. Of the 36 High D/S Ratio Group patients, the average incidence of all cause hospitalization, including terminal hospitalizations, was reduced by 57.1% from a mean admission rate of 1.4 per patient in the year prior to ECP treatment to 0.6 per patient in the following year. The overall incidence of all cause hospitalization, including terminal hospitalizations, in the 130 patient group as a whole was reduced by an average of 70.0% from a mean admission rate of 1.8 per patient in the year prior to ECP treatment to 0.54 per patient in the following year. The differences in hospitalization between all three of the sub-groups and the 130 patient group as a whole were statistically significant (p value <0.01 or less). See Table IV, below.

TABLE IV

Annual Average Number of All Cause Hospital Admissions Per Patient*

| Group | One Yr Prior to ECP Tx | One Yr Post ECP Tx | % Change | p Value |
|---|---|---|---|---|
| Low D/S Ratio (54) | 2.8 ± 1.6 | 0.4 ± .5 | −85.7 | <.0001 |
| Mid D/S Ratio (40) | 2.3 ± 1.4 | 0.4 ± .5 | −82.6 | <.0001 |
| High D/S Ratio (36) | 1.4 ± 1.7 | 0.6 ± .5 | −57.1 | <.01 |
| Overall (130) | 1.8 ± 1.3 | 0.54 ± .5 | −70.0 | <.001 |

*Includes terminal hospitalizations.

At one year after ECP treatment regimen there was observed a significant increase in mean LVEF from baseline as well as a significant reduction from baseline in mean NYHA CHF Class and a significant reduction in the average incidence of hospital admissions.

The foregoing data also indicates that ECP, particularly if administered under the HeartSmart® Graduated™ D/S Ratio ECP Regimen described above, is safe and efficacious for the treatment of congestive heart failure. ECP, administered at Low D/S Ratios, under the above-described regimen, significantly reduced mortality, compared to published data and that of the Mid and High D/S Ratio Groups and the 130 patient group as a whole, and significantly increased left ventricular systolic function, as determined by echocardiography. Such patient benefits may also have a significant impact on the overall treatment costs for heart failure.

Other conditions, in addition to those enumerated hereinabove, which will benefit from the above described Graduated™, Low D/S Ratio ECP Regimen include cardiomyopathy (weakening of the heart muscle of uncertain etiology), heart transplant candidates waiting for a biocompatible donor heart (many of whom die before a biocompatible donor heart becomes available), post-heart transplantation cardiac dysfunction (due to damage to the donor heart in explanation, transit and implantation), post cardiac arrest cardiac dysfunction (due to the absence of blood flow and damage to the heart due to oxygen deprivation), post-acute myocardial infarction cardiac (AMI) dysfunction (due to damage to the heart wall from lack of blood flow and oxygenation) and other forms of left ventricular dysfunction, including without limitation wounds to and infections in the heart. In all of the foregoing, the heart typically cannot effectively eject a sufficient percentage of the blood in the left ventricle. The aforementioned HeartSmart® Graduated™, Low D/S Ratio ECP Regimen can train the heart to beat more synchronously and accept and eject increasing volumes of blood, promote angiogenesis and provide other benefits, safely and effectively treating those conditions.

In addition to conditions related directed to the heart, other ailments that might benefit from increasing the volume of blood ejected from the heart by the aforementioned, Graduated™, Low D/S Ratio ECP Regimen include cognitive deficits, hearing acuity and cognitive or sexual dysfunction. The incidence of septic shock, cardiac arrest, renal failure, stroke or atrial fibrillation in patients might also be decreased through application of the aforementioned, Graduated™ Low D/S Ratio ECP Regimen.

The discussion hereinabove is illustrative but not limiting. Still other variations in treatment parameters are possible within the spirit and scope of the present claims and will readily present themselves to those skilled in the art.

We claim:

1. A method for treating a patient exhibiting left ventricular dysfunction and having a left ventricular ejection fraction of at least 15 percent, which comprises applying, during diastole, for a daily time period of about one-hour, for at least five days each week for at least six weeks, an incrementally increasing external therapeutic pressure using a plurality of cuffs, sequentially to the lower extremities of the patient, beginning with at least one one-hour treatment at a D/S Ratio in the range of about 0.4:1 up to about 0.9:1, followed by at least three one-hour treatments at a D/S Ratio in the range of about 0.5:1 up to about 1:1, and applying the remaining one-hour treatments at a D/S Ratio in the range of about 0.6:1 up to about 1.3:1, until a total of at least 35 one-hour treatments have been delivered.

2. The method in accordance with claim 1 wherein the left ventricular ejection fraction is in the range of 15 percent to about 20 percent applying during diastole, for a time period of at least about one-hour, at least five days each week, for at least six weeks, an incrementally increasing external therapeutic pressure sequentially to said lower extremities of the patient, in the following sequence:

at a therapeutic pressure sufficient to produce a D/S Ratio of about 0.4:1 for at least 1 one-hour treatment;

at a therapeutic pressure sufficient to produce a D/S Ratio of about 0.5:1 for at least the next three one-hour treatments;

at a therapeutic pressure sufficient to produce a D/S Ratio of about 0.6:1 for the next five one-hour treatments;

at a therapeutic pressure sufficient to produce a D/S Ratio of about 0.7:1 for the next ten one-hour treatments; and thereafter at a therapeutic pressure sufficient to produce a D/S Ratio of about 0.8:1 for the remaining one-hour treatments.

3. The method in accordance with claim 1 wherein the left ventricular ejection fraction is in the range of 20 percent to about 30 percent, applying during diastole, for a time period of about one-hour, at least five days each week, for at least six weeks, an incrementally increasing external therapeutic pressure sequentially to said lower extremities of the patient, in the following sequence:

at a therapeutic pressure sufficient to produce a D/S Ratio of about 0.5:1 for at least the first one-hour treatment;

at a therapeutic pressure sufficient to produce a D/S Ratio of about 0.6:1 for at least the next three one-hour treatments;

at a therapeutic pressure sufficient to produce a D/S Ratio of about 0.7:1 for the next five one-hour treatments; and thereafter at a therapeutic pressure sufficient to produce a D/S Ratio of about 0.8:1 for the next ten one-hour treatments; and thereafter at a therapeutic pressure sufficient to produce a D/S Ratio of about 0.9:1 for the remaining one-hour treatments.

4. The method in accordance with claim 1 wherein the left ventricular ejection fraction is in the range of 30 percent to about 40 percent, applying during diastole, for a time period of about one-hour, about five days each week, for at least seven weeks, an incrementally increasing external therapeutic pressure sequentially to said lower extremities of the patient, in the following sequence:

at a therapeutic pressure sufficient to produce a D/S Ratio of about 0.6:1 for at least one one-hour treatment;

at a therapeutic pressure sufficient to produce a D/S Ratio of about 0.7:1 for the next four one-hour treatments;

at a therapeutic pressure sufficient to produce a D/S Ratio of about 0.8:1 for the next five one-hour treatments;

at a therapeutic pressure sufficient to produce a D/S Ratio of about 0.9:1 for the next ten one-hour treatments; and thereafter at a therapeutic pressure sufficient to produce a D/S Ratio of about 1:1 for the remaining one-hour treatments.

5. The method in accordance with claim 1 wherein the left ventricular ejection fraction is in the range of 40 percent to about 50 percent, applying during diastole, for a time period of about one-hour, about five days each week, for at least seven weeks, an incrementally increasing external therapeutic pressure sequentially to said lower extremities of the patient, in the following sequence:

at a therapeutic pressure sufficient to produce a D/S Ratio of about 0.7:1 for at least one one-hour treatment;

at a therapeutic pressure sufficient to produce a D/S Ratio of about 0.8:1 for at least the next three one-hour treatments;

at a therapeutic pressure sufficient to produce a D/S Ratio of about 0.9:1 for the next five one-hour treatments;

at a therapeutic pressure sufficient to produce a D/S Ratio of about 1:1 for the next ten one-hour treatments; and thereafter at a therapeutic pressure sufficient to produce a D/S Ratio of about 1.1:1 for the remaining one-hour treatments.

6. The method in accordance with claim 1 wherein the left ventricular ejection fraction is in greater than about 50 percent, applying during diastole, for a time period of about one-hour, about five days each week, for at least seven weeks, an incrementally increasing external therapeutic pressure sequentially to said lower extremities of the patient, in the following sequence:

at a therapeutic pressure sufficient to produce a D/S Ratio of about 0.9:1 for at least one one-hour treatment;

at a therapeutic pressure sufficient to produce a D/S Ratio of about 1:1 for at least the next three one-hour treatments;

at a therapeutic pressure sufficient to produce a D/S Ratio of about 1.1:1 for the next five one-hour treatments;

at a therapeutic pressure sufficient to produce a D/S Ratio of about 1.2:1 for the next ten one-hour treatments; and thereafter at a therapeutic pressure sufficient to produce a D/S Ratio of about 1.3:1 for the remaining one-hour treatments.

7. A method in accordance with claim 1 wherein the increased external therapeutic pressure is applied sequentially first to the calves, next to the thighs and then to the buttocks of the patient.

8. The method in accordance with claim 1 wherein the applied external therapeutic pressure does not exceed 240 millimeters of mercury.

9. The method in accordance with claim 1 applied to a patient suffering from a condition selected from the group consisting of congestive heart failure, angina, acute myocardial infarction, cardiogenic shock, ischemic stroke, cardiomyopathy, post-heart transplant cardiac dysfunction, post-cardiac arrest, cardiac rhythm dysfunction, heart trauma, heart infection, post-acute myocardial infarction dysfunction, acute renal failure, acute hepatic failure, peripheral artery disease, edema, cognitive deficits, hearing acuity, and sexual dysfunction.

10. The method in accordance with claim 1 further comprising the step of monitoring a patient's ventilation efficiency of $CO_2$ by measuring at least one of ($VE/VCO_2$) slope, heart rate recovery time (bpm) after exercise (HRRtX), peak volume of $O_2$ ($pVO_2$), oxygen efficiency (OE) and chronotropic response index (CRI).

11. The method for treating a patient exhibiting left ventricular dysfunction and having a left ventricular ejection fraction of at least 15 percent which comprises applying, during diastole, for a time period of about one-hour, about five days each week for at least seven weeks, an incrementally increasing external therapeutic pressure sequentially to the lower extremities of the patient, wherein a D/S Ratio is derived from the patient's left ventricular ejection fraction, and the initial set of hourly treatments is applied at the derived D/S Ratio, the next set of hourly treatments is applied to achieve the derived D/S Ratio plus 0.1, the following set of hourly treatments is applied to achieve the derived D/S Ratio plus 0.2, followed by a set of hourly treatments applied to achieve the derived D/S Ratio plus 0.3 and the remaining hourly treatments are applied to achieve the derived D/S Ratio plus 0.4.

12. The method in accordance with claim 11 applied to a patient suffering from a condition selected from the group consisting of congestive heart failure, angina, acute myocardial infarction, cardiogenic shock, ischemic stroke, cardiomyopathy, post-heart transplant cardiac dysfunction, post-cardiac arrest, cardiac rhythm dysfunction, heart trauma, heart infection, post-acute myocardial infarction dysfunction, acute renal failure, acute hepatic failure, peripheral artery disease, edema, cognitive deficits, hearing acuity, and sexual dysfunction.

13. A method for treating a CHF patient exhibiting left ventricular dysfunction and having a left ventricular ejection fraction of at least 15% to 50%, which comprises applying, during diastole, for a time period of about one-hour, at least five days each week for at least about six weeks an incrementally increasing external therapeutic pressure by sequentially inflating bladders disposed within at least two cuffs removably fastened about the calves, thighs and buttocks of the patient, beginning with at least the first one-hour treatment at a D/S Ratio in the range of about 0.4:1 to about 0.7:1, for at least the next three one-hour treatments at a D/S Ratio in the range of about 0.5:1 to about 0.8:1, the next five one-hour treatments at a D/S Ratio in the range of about 0.6:1 to about 0.9:1, the next ten one-hour treatments at a D/S Ratio in the range of about 0.7:1 to about 1:1, and the remaining one-hour treatments at a D/S Ratio in the range of about 0.8:1 to about 1.1:1, until a total of at least 35 one-hour treatments have been delivered.

14. A method of treating a patient having an impaired cardiopulmonary function which comprises applying sequentially, during diastole, for a time period of about one hour, about five days a week for at least seven weeks, an incrementally increasing therapeutic pressure to the lower extremities of the patient at a selected D/S Ratio of at least 0.4 for at least one hourly treatment, at the selected D/S Ratio plus 0.1 for at least the next three hourly treatments, at the selected D/S Ratio plus 0.2 for the next five hourly treatments, at the selected D/S Ratio plus 0.3 for the next ten hourly treatments, and at the selected D/S Ratio plus 0.4 for the remaining hourly treatments.

15. The method in accordance with claim 14 wherein the impaired cardiopulmonary function is indicated by at least one of the following indicia: a $VE/VCO_2$ slope of at least 37 degrees, a heart rate recovery time of less than 17 beats per minute, an oxygen efficiency of less than 1.7, a peak oxygen volume of less than 7.4 milliliters per beat, chronotropic response index of less than 0.8

16. A method of treating a patient who exhibits at least one of the following: a $VE/VCO_2$ slope of at least 37 degrees, a heart rate recovery time of less than 17 beats per minute, an oxygen efficiency of less than 1.7, a peak oxygen volume of less than 7.4 milliliters per beat, chronotropic response index of less than 0.8 which comprises periodically applying, during diastole, sequentially to at least two of the patient's calves, then thighs and then buttocks, an incrementally increasing therapeutic pressure, based upon the patient's left ventricular ejection fraction, in a series of treatments, each said treatment having a duration of one hour.

17. The method in accordance with claim 16 wherein said therapeutic pressure is applied for one-hour per day five days a week.

18. The method in accordance with claim 16 wherein the therapeutic pressure is increased after each one-hour treatment.

19. The method in accordance with claim 16 wherein the therapeutic pressure is increased after two one-hour treatments.

20. The method in accordance with claim 16 wherein the therapeutic pressure is increased after three one-hour treatments.

21. The method in accordance with claim 16 wherein the therapeutic pressure is increased after three one-hour treatments.

22. The method in accordance with claim 16 wherein the therapeutic pressure is increased after five one-hour treatments.

23. The method in accordance with claim 16 wherein the therapeutic pressure is increased after ten one-hour treatments.

24. The method in accordance with claim 16 wherein the therapeutic pressure is increased after 15 one-hour treatments.

* * * * *